United States Patent
Poo et al.

(10) Patent No.: US 6,833,270 B2
(45) Date of Patent: Dec. 21, 2004

(54) APPARATUS AND METHOD FOR ISOLATING CELLS FROM ORGANS

(75) Inventors: Ramon E. Poo, Miami, FL (US); Camillo Ricordi, Miami, FL (US)

(73) Assignees: Biorep Technologies, Inc., Miami, FL (US); The University of Miami, Miami, FL (US)

( * ) Notice: Subject to any disclaimer, the term of this patent is extended or adjusted under 35 U.S.C. 154(b) by 183 days.

(21) Appl. No.: 09/994,445

(22) Filed: Nov. 27, 2001

(65) Prior Publication Data

US 2003/0100105 A1 May 29, 2003

(51) Int. Cl.⁷ .................................................. C12N 5/00
(52) U.S. Cl. ........................ 435/377; 435/378; 435/379; 435/380; 435/381
(58) Field of Search ................................. 435/377, 378, 435/379, 380, 381

(56) References Cited

U.S. PATENT DOCUMENTS

| | | | |
|---|---|---|---|
| 4,017,361 A | * | 4/1977 | Febvre ........................ 435/366 |
| 5,079,160 A | | 1/1992 | Lacy et al. |

* cited by examiner

*Primary Examiner*—Leon B. Lankford, Jr.
(74) *Attorney, Agent, or Firm*—Akerman Senterfitt

(57) ABSTRACT

An apparatus and method for extracting cells from organs in which a digestion chamber includes at least one inlet and at least one outlet, and a separator for retaining the organ and permitting the cells and the physiologically compatible medium to exit the outlet. The digestion chamber can also includes at least one agitation member having an interior with at least one void. An agitation member for extracting cells from organs is also disclosed.

18 Claims, 4 Drawing Sheets

US 6,833,270 B2

APPARATUS AND METHOD FOR ISOLATING CELLS FROM ORGANS

FIELD OF INVENTION

This invention relates generally to an apparatus and method for isolating cells from organs.

BACKGROUND OF INVENTION

Scientists are currently researching possible applications for isolated cells from parent organs, such as the liver, spleen, kidney, adrenal, and pancreas. Some research that has been conducted on the clinical application of isolated cells has involved groups of cells called the Islets of Langerhans that have been isolated from the pancreas. An application for the Islet of Langerhans cells is as a treatment for diabetic patients. Patients with diabetes have Islets of Langerhans that do not function properly, and therefore, do not produce enough insulin. Some clinical research is aimed at developing a procedure for transplanting functioning Islets of Langerhans into diabetic patients to restore the insulin producing ability of the pancreas. Clinical research of such requires isolated Islet of Langerhans cells, but these cells must be isolated while still viable. Viable isolated cells are mostly obtained from organs of the very recently deceased. The apparatus and method for isolating the cells should be able to extract isolated cells with as little damage to the cells as possible.

Many different methods and approaches have been attempted to isolate individual cells from their respective parent organs. Prior methods have produced isolated cells with some cell destruction. This cell destruction can result from the relatively severe mechanical stimulation that is used to isolate cells from an organ.

One method that attempts to overcome the loss of damaged cells due to relatively severe mechanical stress is described in U.S. Pat. No. 5,079,160, to Lacy, et al. The method disclosed by Lacy, et al. comprises the steps of: placing an organ or a piece of an organ in a digestion chamber along with marble agitators; distending the organ or a piece of the organ with physiologically compatible medium containing a protease; continuously recirculating that medium; and separating the isolated cells. The marble agitators greatly increase the amount of undamaged cells obtained through isolation without reducing the quality of the isolated cells obtained by gently agitating the organ. Moreover, the marbles are an appropriate size, weight, and density for obtaining beneficial results as compared to other agitators of varying size, weight, and density which can cause severe mechanical disruption of the organ tissue resulting in some cells being destroyed.

Although the Lacy, et al. method produces isolated cells in relatively high concentrations, the use of marble agitators has significant disadvantages. The marble agitators do not have a high level of hardness. Also, the marble agitators can be brittle or become brittle and can break, fracture, or chip during the isolation of cells. Furthermore, due to stringent sterilization standards, the marble agitators must undergo relatively stressful sterilization procedures in which the marble agitators may become brittle, break, fracture, or chip.

SUMMARY OF THE INVENTION

The present invention relates to an apparatus for extracting cells from organs. The apparatus includes a digestion chamber that contains a physiologically compatible medium with at least one protease. The digestion chamber has at least one inlet and at least one outlet, and has a separator means for retaining the organ and permitting the cells and the physiologically compatible medium to exit the outlet. The apparatus also has at least one agitation member in the digestion chamber, and the agitation members have an interior with at least one void.

In one embodiment, the agitation members can include a non-corrosive metal and a substantially smooth, continuous exterior surface, and can be substantially spherical. The agitation members can also have an interior with one centrally located substantially spherical void. Additionally, the agitation members can have a density of about 3.0–4.0 g/cm$^3$.

Moreover, the agitation members can have a density of about 3.5 g/cm$^3$.

Furthermore, the present invention relates to agitation members for the digestion chamber of an apparatus for extracting cells from organs. The agitation members have an interior with at least one void. Additionally, the agitation members can have the characteristics listed above.

The present invention also relates to a method for extracting cells from an organ. The method includes the steps of: providing a physiologically compatible medium with at least one protease; providing a digestion chamber, the chamber having at least one inlet and at least one outlet, and a separator for retaining the organ and for permitting the cells and the physiologically compatible medium to exit the outlet; providing at least one agitation member in the digestion chamber, the agitation members having an interior with at least one void; flowing the physiologically compatible medium through the digestion chamber; moving the agitation members within the digestion chamber, whereby the agitation members will agitate the organ to facilitate release of the cells; and collecting the cells. In regard to the step of moving the agitation members, the method can further include a step of moving the digestion chamber so as to move the agitation members within the digestion chamber. The agitation members can also have a density of 3.0–4.0 g/cm$^3$, and can have a density of 3.5 g/cm$^3$.

The invention can also relate to a method for extracting cells from an organ in which the organ is a pancreas and the cells are Islet of Langerhans. Also, the protease in the physiologically compatible medium can be collagenase. In one aspect, the physiologically compatible medium can be heated prior to entering the digestion chamber to a temperature selected to maximize the effectiveness of the protease. Therefore, in one aspect, the heating can heat the physiologically compatible medium to a temperature of 24° C.–40° C. In yet another aspect, the physiologically compatible medium can be heated to a temperature of 37° C. The physiologically compatible medium can also be cooled following exit from the outlet of the digestion chamber to a temperature between 4° C.–20° C. Additionally, prior to the step of collecting the cells, the method can include a step of detecting the cells in the physiologically compatible medium. The method can also include the step of removing the physiologically compatible medium containing the cells and adding additional physiologically compatible medium without heating prior to entering the digestion chamber.

BRIEF DESCRIPTION OF THE DRAWINGS

There are shown in the drawing embodiments which are presently preferred, it being understood, however, that the invention is not limited to the precise arrangements and instrumentalities shown, wherein.

DETAILED DESCRIPTION OF THE PREFERRED EMBODIMENTS

Figure 1:
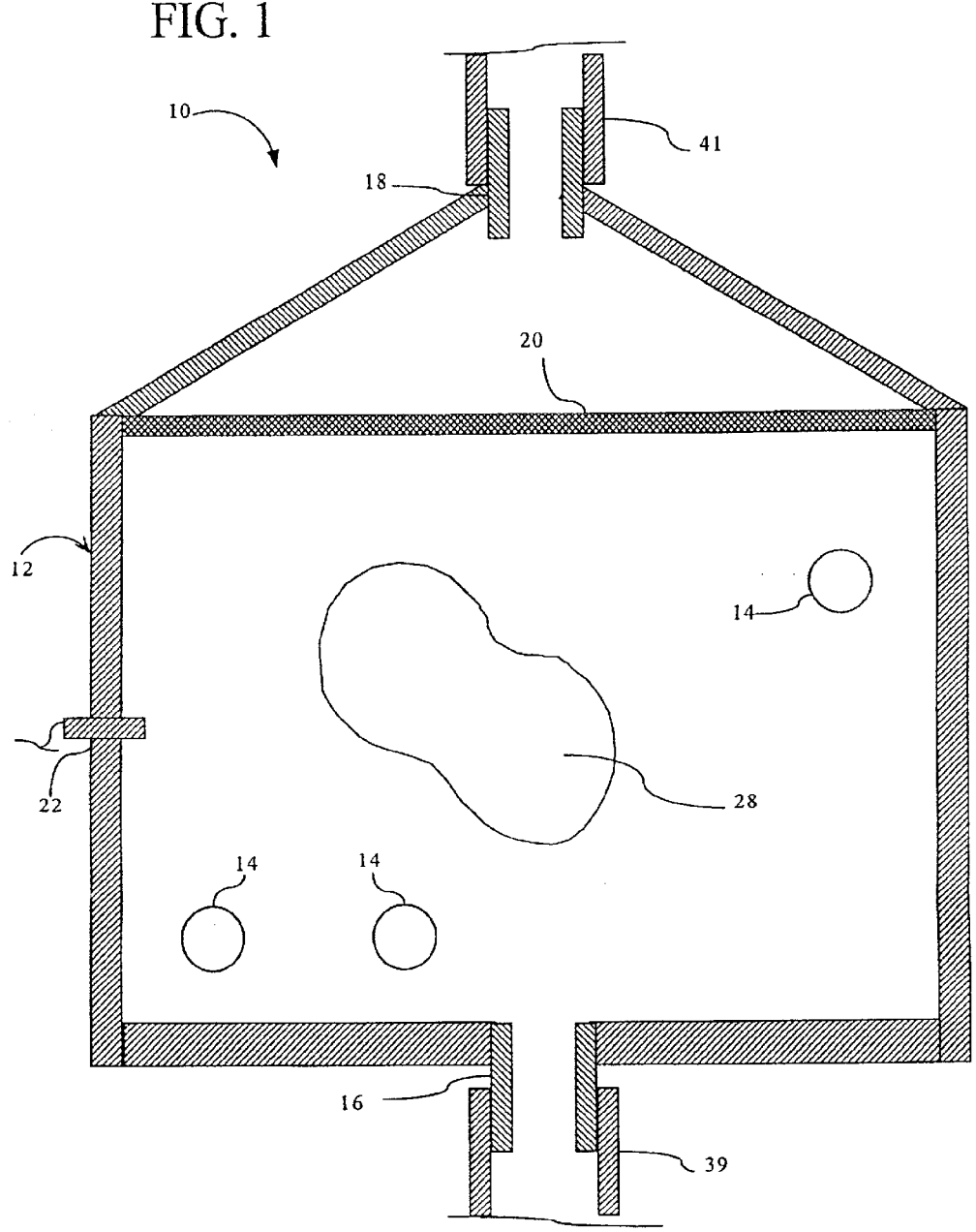
FIG. 1 is a cross-sectional diagram of one embodiment of the digestion chamber.

The invention encompasses methods and apparatuses for extracting cells from organs 28. As illustrated in FIG. 1, the apparatus 10 includes a digestion chamber 12 that contains a physiologically compatible medium with at least one protease. The digestion chamber 12 also has at least one inlet 16 to allow for physiologically compatible medium to enter the digestion chamber 12, and at least one outlet 18 to allow for physiologically compatible medium and cells to exit the digestion chamber 12. The digestion chamber 12 also has a separator 20 for retaining an organ 28 and permitting the cells and the physiologically compatible medium to exit at least one outlet 18. The digestion chamber 12 also has at least one agitation member 14.

In one embodiment as illustrated in FIG. 1, the separator 20 can be a screen with suitably sized pores to allow the physiologically compatible medium and the cells to exit the digestion chamber 12 while retaining the organ 28 in the digestion chamber 12. In use of a screen, the size of the pores relates directly to the size of the cells being isolated; moreover, the size of the pores may be different for isolating cells from different organs 28. However, the invention is not limited to using a screen as a separator 20 as other separators 20 can be used. In one aspect, a plate with pores dimensioned to permit fluid and cell flow through the plate, while retaining the organ 28, can be used in the place of the screen.

Figure 2:
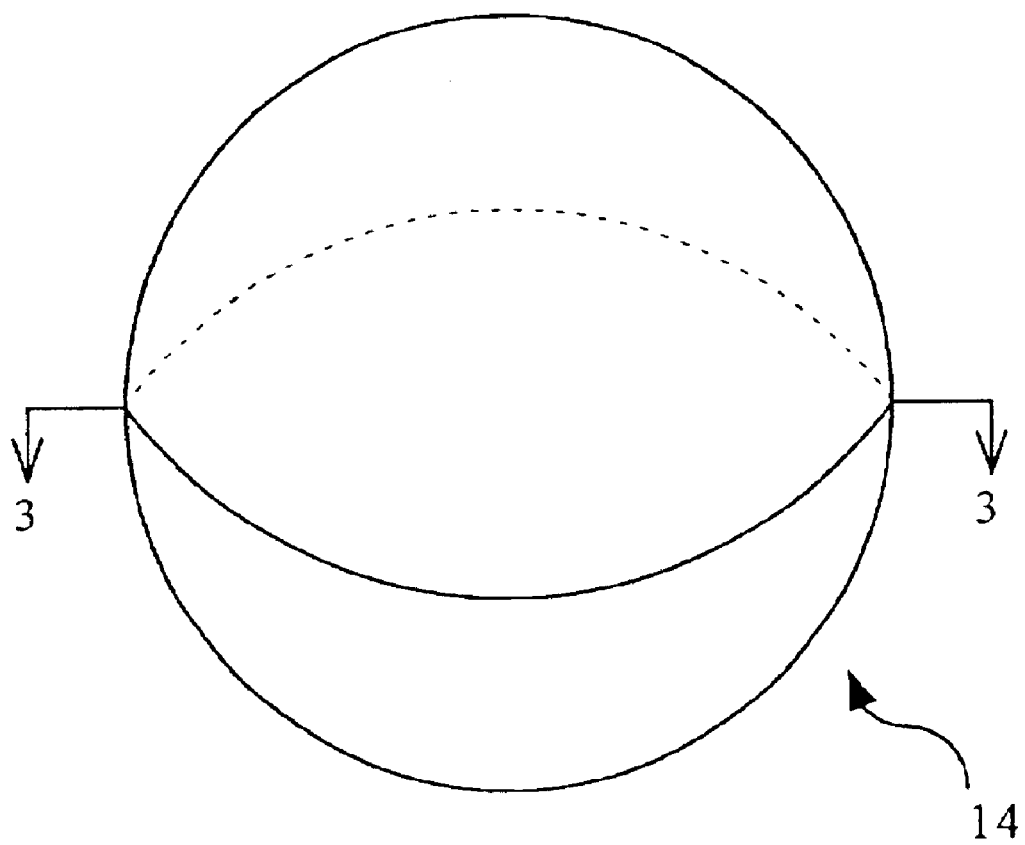
FIG. 2 is a side elevation of an agitation member.
Figure 3:
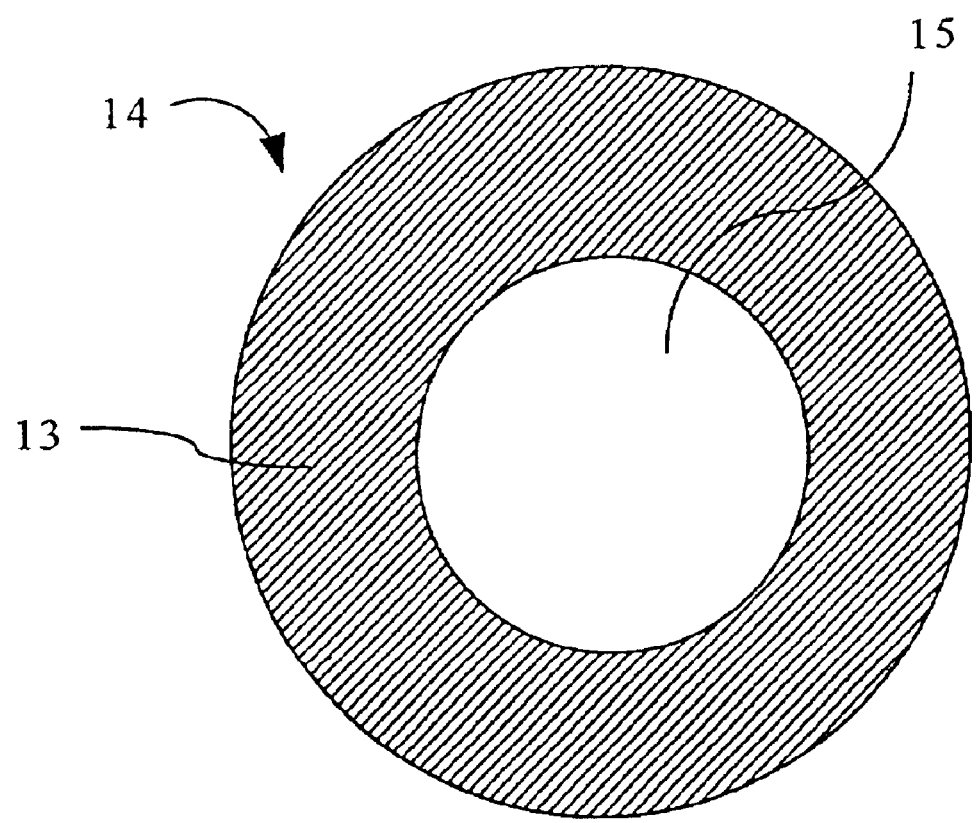
FIG. 3 is a cross-sectional view of an agitation member taken along line 3—3 in FIG. 2.

FIG. 2 and FIG. 3 illustrate a whole agitation member 14 and a cross-sectional view of an agitation member 14, respectively. The agitation members 14 can be relatively small compared to the digestion chamber 12, as larger agitation members 14 may not move freely to agitate the organ 28 or may consequently weigh relatively more and cause damage to the cells. As illustrated in FIG. 3, an agitation member 14 has an interior 13 with at least one void 15. While FIG. 3 illustrates the agitation member 14 with the interior 13 having one void 15, an agitation member 14 can include an interior 13 with a plurality of voids 15. Furthermore, in an embodiment of an agitation member 14 having an interior 13 with only one void 15, the void 15 can be substantially spherical and centrally located, providing the agitation member 14 with a center of mass located at the intersection of any two diameters of the void 15. A substantially spherical agitation member 14 with such a center of mass can exhibit pure rotation. Pure rotation, the motion of a rigid body whose orientation in space changes, but whose center of mass remains fixed, may be more desirable than a rotation characterized by a wobble because an agitation member 14 with a pure rotation may provide a more gentle agitation to the organ 28 and prevent cell damage.

In one embodiment, the agitation members 14 can have a density of about 3.0–4.0 g/cm$^3$. For example, the agitation members 14 can have a density of about 3.5 g/cm$^3$. The density of the agitation member 14 is computed by dividing the mass of the agitation member 14 by the total volume encompassed by the exterior surface. The measured total volume encompassed by the exterior surface includes the volume of the interior 13 represented by the voids 15.

In one embodiment, the agitation members 14 can include a non-corrosive metal. An agitation member 14 coated with or made from a non-corrosive metal can be especially durable after prolonged contact with heat and moisture, and during sterilization when the agitation members 14 are subjected to extreme heat. Furthermore, the non-corrosive metal provides a hardness to the agitation members 14 that is beneficial. The level of hardness allows the agitation members 14 to be resistant to deformation, chipping, and cracking, while colliding with the walls of the digestion chamber 12 and with each other. In one aspect, the non-corrosive metal is stainless steel. However, the invention is not limited in this regard as the agitation members 14 can include other materials which do not react with the cells or with the physiologically compatible medium. The agitation members 14 can also include a substantially smooth, continuous exterior surface. An agitation member 14 including a substantially smooth, continuous exterior surface can also provide advantages during sterilization as discontinuities in the surface provide locations for accumulations of dirt and bacteria which are difficult to clean and sterilize. However, the invention is not limited in this regard as a non-continuous exterior surface can be used.

In another embodiment, the agitation members 14 can be substantially spherical. A substantially spherical agitation member 14 can be advantageous because the spherical shape allows the agitation member 14 to help release cells from the organ 28 without severe mechanical disruption. Furthermore, severe mechanical disruption, which may be produced by agitation members 14 with edges, can damage or destroy some cells during the cell isolation. However, although a substantially spherical agitation member 14 can be advantageous, the invention is not limited in this regard as other shaped agitation members 14 may be used.

Additionally, the combined attributes of the agitation members 14 discussed above can have beneficial synergistic effects. While the non-corrosive metal provides hardness, durability, and an easily sterilized surface, the agitation member 14 can still have a relatively light mass, which can be beneficial for gentle agitation, because of the interior 13 with at least one void 15. A solid agitation member 14 of similar dimensions and made from the same material would have a much greater mass and thus a greater density. The resulting agitation member 14 may not be capable of gentle agitation. Furthermore, the continuous exterior surface of the agitation members 14 can also facilitate gentle agitation, as it lacks edges and also does not compromise sterilization.

In another aspect, the digestion chamber 12 can be of a suitable size to hold whole organs 28 or large pieces of organs 28, or can be a smaller size to contain small pieces of organs 28. The digestion chamber 12 can also include any number of monitoring sensors, such as a thermocouple 22, or any other suitable means for measuring temperature, as it may be beneficial to measure the temperature inside the digestion chamber 12. The temperature can also be measured outside of the chamber 12.

Figure 4:
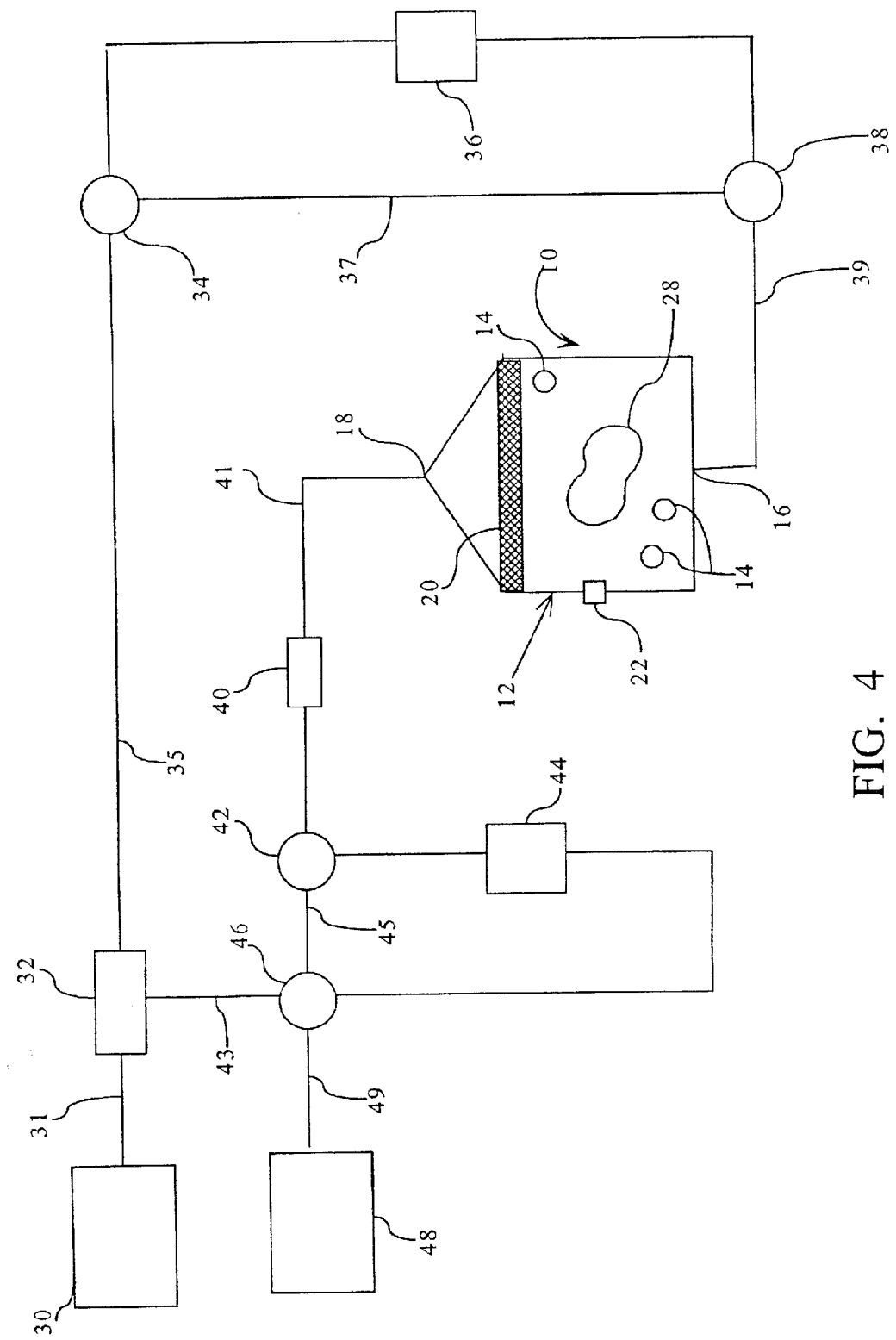
FIG. 4 is a schematic illustration of a system for isolating cells from an organ.

A system for isolating cells from organs 28 is shown in FIG. 4. In FIG. 4, the apparatus 10 is shown with the digestion chamber 12 having inlet 16 and outlet 18. The digestion chamber 12 can be connected to a recirculating system as shown in FIG. 4; however, the method is not limited to a recirculating system as a non-recirculating system can be used and may even be advantageous in some situations.

In overview, in one method for isolating cells from organs 28, the user provides an organ 28 in a digestion chamber 12 containing a physiologically compatible medium with at least one protease. The physiologically compatible medium can flow through the inlet 16, the digestion chamber 12, and exit through the outlet 18. The digestion chamber 12 can include a separator 20 that permits the physiologically compatible medium and the isolated cells to exit the digestion chamber 12 while retaining the organ 28 inside the digestion chamber 12. At least one agitation member 14 with an interior 13 having at least one void 15 is provided in the digestion chamber 12. The agitation members 14 are moved with the digestion chamber 12 to agitate the organ 28 and facilitate the release of the cells. In one embodiment of the method, the agitation members 14 are moved by gently shaking the digestion chamber 12. Finally, the isolated cells are collected.

In a system for recirculating the physiologically compatible medium as shown in FIG. 4, the physiologically compatible medium can be heated prior to entering the digestion chamber 12. Before the physiologically compatible medium is introduced to the digestion chamber 12, a pump 32 can pump the physiologically compatible medium first through a conduit 35 to a heating device 36. The physiologically compatible medium can be heated by the heating device 36 through any suitable means. The physiologically compatible medium can be heated to a temperature selected to maximize the effect of the protease. As is known in the art, the catalytic rate of a protease can be improved within a range of temperatures; therefore, the temperature selected to heat the physiologically compatible medium can be dependent on a variety of factors, including the specific protease or combination of proteases used. Accordingly, physiologically compatible medium can be heated to a temperature between 24° C.–40° C. For example, the physiologically compatible medium can be heated to about 37° C.; however, the method is not limited in this regard, as a combination of factors are used to determine the temperature to which to heat the physiologically compatible medium.

After the physiologically compatible medium is heated to the proper temperature, physiologically compatible medium can be flowed through conduit 39 into the digestion chamber 12 through the inlet 16. The physiologically compatible medium with at least one protease can isolate the cells from the organ 28. To facilitate the release of isolated cells, the agitation members 14 are moved, for example, by shaking the digestion chamber 12, so as to gently agitate the organ 28.

The physiologically compatible medium exits the digestion chamber 12 through outlet 18 and conduit 41. The physiologically compatible medium can then be cooled. The physiologically compatible medium can be cooled by any suitable means, such as by flowing the physiologically compatible medium through a cooling device 44. The physiologically compatible medium can be cooled to a temperature between 4° C.–20° C. The cooling of the physiologically compatible medium can slow the activity of the protease, and therefore, prevent damage to any of the isolated cells that have been released from the organ 28 and may be suspended in the physiologically compatible medium. However, the physiologically compatible medium can also bypass the cooling device 44 by manipulating valve 42 and flowing physiologically compatible medium through conduit 45 to valve 46.

Furthermore, after the physiologically compatible medium exits the digestion chamber 12, the user can monitor the physiologically compatible medium for the presence of isolated cells, such as at a sampling port 40. Once the user detects isolated cells, the physiologically compatible medium containing the isolated cells should not be re-circulated to the digestion chamber 12. The valve 46 can be used to direct the physiologically compatible medium containing isolated cells through a conduit 49 to a collector 48. Valve 46 can be used to direct the physiologically compatible medium that does not contain isolated cells through conduit 43 to be re-circulated.

Additional physiologically compatible medium, such as in container 30, can be added to the system through conduit 31 and eventually to the digestion chamber 12 to facilitate the release of the cells from the organ 28. However, in another arrangement, the additional physiologically compatible medium may be added directly to the digestion chamber 12. The additional physiologically compatible medium can also be heated prior to entering the digestion chamber 12 by flowing the physiologically compatible medium to the heating device 36; however, by manipulating valve 34 and valve 38, the additional physiologically compatible medium can bypass the heating device 36.

The invention is capable of taking other forms and embodiments without departing from the spirit of the invention, and reference should therefore be made to the following claims, rather than the forgoing specification, as indicating the scope of the invention.

We claim:

1. A method for extracting cells from an organ, comprising the steps of:
    providing a physiologically compatible medium with at least one protease;
    providing a digestion chamber, said chamber having at least one inlet and at least one outlet, and a separator for retaining said organ and permitting said cells and said physiologically compatible medium to exit said outlet;
    providing at least one agitation member in said digestion chamber, said agitation member comprising a hard, thermally stable material and having an interior with at least one void and an average density of between about 3.0–4.0 cm$^3$;
    flowing said physiologically compatible medium through said digestion chamber;
    moving said agitation member within said digestion chamber, whereby said agitation member will agitate said organ to facilitate release of said cells; and
    collecting said cells.

2. The method of claim 1, wherein the step of moving said agitation member further comprises a step of moving said digestion chamber so as to move said agitation member within said digestion chamber.

3. The method of claim 1, wherein said agitation member comprises non-corrosive metal.

4. The method of claim 1, wherein said agitation member comprises a substantially smooth, continuous exterior surface.

5. The method of claim 1, wherein said agitation member is substantially spherical.

6. The method of claim 5, wherein said agitation member has an interior with one centrally located substantially spherical void.

7. The method of claim 1, wherein said agitation member has a density of about 3.0–4.0 g/cm$^3$.

8. The method of claim 1, wherein said agitation member has a density of about 3.5 g/cm$^3$.

9. The method of claim 1, wherein said protease is collagenase.

10. The method of claim 1, wherein said organ is a pancreas and said cells are Islets of Langerhans.

11. The method of claim 1, wherein said physiologically compatible medium is heated prior to entering said digestion chamber.

12. The method of claim 1, wherein said physiologically compatible medium is heated to a temperature selected to maximize the effectiveness of the protease.

13. The method of claim 1, wherein said heating heats said physiologically compatible medium to a temperature between 24° C.–40° C.

14. The method of claim 1, wherein said heating heats said physiologically compatible medium to a temperature of about 37° C.

15. The method of claim 1, wherein said physiologically compatible medium is cooled following exit from said outlet of said digestion chamber.

16. The method of claim 1, wherein said cooling cools said physiologically compatible medium to a temperature between 4° C.–20° C.

17. The method of claim 1, wherein prior to said step of collecting said cells, further comprising a step of detecting said cells in said physiologically compatible medium.

18. The method of claim 1, further comprising a step of removing said physiologically compatible medium containing said cells, and adding additional physiological compatible medium without heating prior to entering said digestion chamber.

* * * * *